United States Patent
Osei-Gyimah

(10) Patent No.: US 6,207,828 B1
(45) Date of Patent: Mar. 27, 2001

(54) PROCESS FOR MAKING 2-(TRIHALOACETYL)-3-(SUBSTITUTED AMINO)-2-PROPENOATES

(75) Inventor: Peter Osei-Gyimah, Horsham, PA (US)

(73) Assignee: Rolm and Haas Company, Philadelphia, PA (US)

(*) Notice: Subject to any disclaimer, the term of this patent is extended or adjusted under 35 U.S.C. 154(b) by 0 days.

(21) Appl. No.: 09/433,249

(22) Filed: Nov. 4, 1999

Related U.S. Application Data

(60) Provisional application No. 60/107,796, filed on Nov. 10, 1998.

(51) Int. Cl.[7] ............... C07C 229/00; C07C 233/00; C07D 279/12; C07D 265/30; C07D 207/04
(52) U.S. Cl. .................. 544/56; 544/171; 546/248; 548/573; 548/341.3; 560/170; 564/197; 562/567
(58) Field of Search .................. 564/197; 560/170; 562/567; 544/56, 171; 546/248; 548/573, 341.5

(56) References Cited

PUBLICATIONS

Kraj et al., J.Heterocyclic Chem., 34, 247 (1997), Nov. 1997.*
Welch et al., editors, "Fluorine in Bioorganic Chemistry" John Wiley & Sons, New York, NY (1991), Nov. 1997.*
Adbulla et al., "The Chem.of Formamide Acetals",Tetrahedron 67, #35, 1675–1735 (1975), Nov. 1997.*

* cited by examiner

Primary Examiner—Mukund J. Shah
Assistant Examiner—Sudhaker B. Patel
(74) Attorney, Agent, or Firm—Clark R. Carpenter

(57) ABSTRACT

This invention provides a convenient, new, one step process for the preparation of 2-(trihaloacetyl)-3-(substituted amino)-2-propenoates and related derivatives thereof by reaction of carbonyl compounds substituted with a trihaloacetyl group with an acetal in the presence of an organic acid. The resulting propenoates are useful as intermediates for the construction of trihalomethyl substituted heterocyclic compounds for use in pharmaceutical and agricultural applications.

10 Claims, No Drawings

PROCESS FOR MAKING 2-(TRIHALOACETYL)-3-(SUBSTITUTED AMINO)-2-PROPENOATES

This application claims for domestic priority Provisional Patent Application Ser. No. 60/107,796 filed Nov. 10, 1998.

This invention relates to a new and convenient one step process for the preparation of 2-(trihaloacetyl)-3-(substituted amino)-2-propenoates and related derivatives thereof. These compounds are useful intermediates in the synthesis of trihalomethyl substituted heterocycles for pharmaceutical and agricultural applications.

It is known that N,N-dimethylamino derivatives are useful intermediates in organic synthesis, for example Burnett et al., *Heterocycles*, 45 (1997) and Kralj et al., *J. Heterocyclic Chem.*, 34, 247 (1997). In particular, N,N-dimethylamino-methylene derivatives (1) of β-ketoesters have been utilized in the synthesis of substituted heterocyclic compounds, many of which have important pharmaceutical and agricultural applications, for example Gelin et al., *Synthesis*, 566 (1983) and Mosti et al., *Farmaco*, 47, 427 (1992).

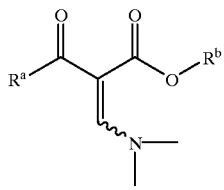

1

$R^a$ = Alkyl, Alkenyl, Aryl
$R^b$ = Alkyl

It also has been recognized that trifluoromethyl ($CF_3$) groups can significantly modify the physico-chemical properties and the biological activities of compounds on which they are substituted, for example Banks et al., editors, "Organofluorine Chemistry, Principles and Applications", Plenum Press, New York, N.Y. (1994) and Welch et al., editors, "Fluorine in Bioorganic Chemistry", John Wiley and Sons, New York, N.Y. (1991). Therefore, the availability of the N,N-dimethylaminomethylene derivative (2) of ethyl trifluoroacetoacetate (3) would serve as a simple, but key intermediate for the construction of trifluoromethyl substituted heterocycles for pharmaceutical and agricultural applications.

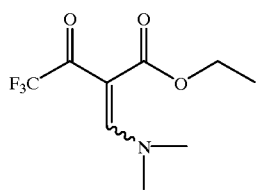

2

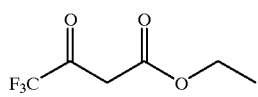

3

Dimethylformamide (DMF) acetals have many functions in synthetic organic chemistry with one of the functions being the formation of N,N-dimethylaminomethylene derivatives with activated alkyl positions, for example Abdulla et al., *Tetrahedron*, 35, 1675 (1975). Thus, ethyl acetoacetate, Scheme 1, readily reacts at the active methylene site with DMF dimethylacetal to produce the N,N-dimethylaminomethylene derivative in good yields, for example Beck et al., *J. Heterocyclic Chem.*, 24, 693 (1987).

Scheme 1

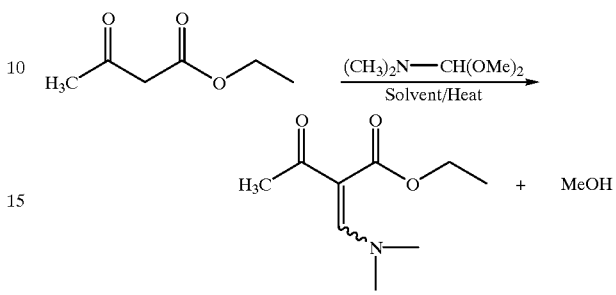

Although N,N-dimethylaminomethylene derivative of various β-ketoesters have been reported in the literature, the preparation of such a derivative from ethyl trifluoroacetoacetate (3) has not been successful. In fact, the reaction of (3) and DMF acetal has been reported to yield an undesirable product without the isolation of 2, for example Beck et al., *J. Heterocyclic Chem.*, 24, 739 (1987). Accordingly, compound (2) has not been available for the synthesis of biologically useful, trifluoromethyl substituted heterocycles and it is not commercially available.

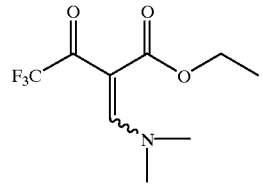

2

I have found surprisingly conditions which allow the preparation of ethyl 2-trifluoroacetyl-3-(N,N-dimethylamino)-2-propenoate (2) from ethyl trifluoroacetoacetate and DMF acetals according to a general one-step reaction. Specifically, I found that compound 2 can be prepared in good yields (61–85%) by reacting ethyl trifluoroacetoacetate with DMF acetals in the presence of an organic acid such as acetic acid. While not wishing to be bound by theory, the success of this reaction condition appears to lie in the suppression of the loss of the trifluoroacetyl group from (2) through the attack of the alcohol by-products. In the absence of the organic acid, ethyl 3-(N,N-dimethylamino)-2-propenoate (4) is formed as the major product in all cases. My overall result is shown in Scheme 2.

Scheme 2

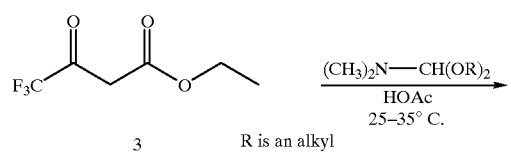

3   R is an alkyl

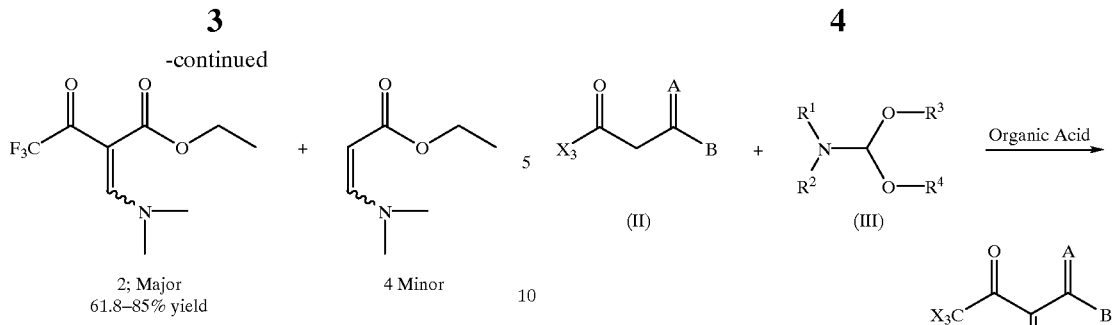

2; Major
61.8–85% yield

4 Minor

My result is especially surprising in view of the results reported by Beck et al., vide supra, who attempted to prepare (2) by reacting ethyl trifluoroacetoacetate with DMF dimethyl acetal in the presence of a catalytic quantity of p-toluenesulfonic acid. The reaction resulted in the formation of ethyl 3-(N,N-dimethylamino)-2-propenoate (4) in 75% yield. Presumably, the methanol by-product further reacted with the target compound (2) to give the unexpected product and methyl trifluoroacetate.

The only other route leading to a N,N-dialkylaminomethylene derivative of ethyl trifluoroacetoacetate reported in the literature is by Bartnik, et al., *Tet. Letters* 33, 8751 (1996). These workers prepared ethyl 2-trifluoroacetyl-3-(N,N-diisopropylamino)-2-propenoate (6) as shown in Scheme 3. This was accomplished not by the one-step β-ketoester/DMF acetal reaction, but in two steps by converting the ketoester to the chloroacrolein (5) under Vilsmeier conditions and then treating this intermediate with diisopropylamine to give 6.

Scheme 3

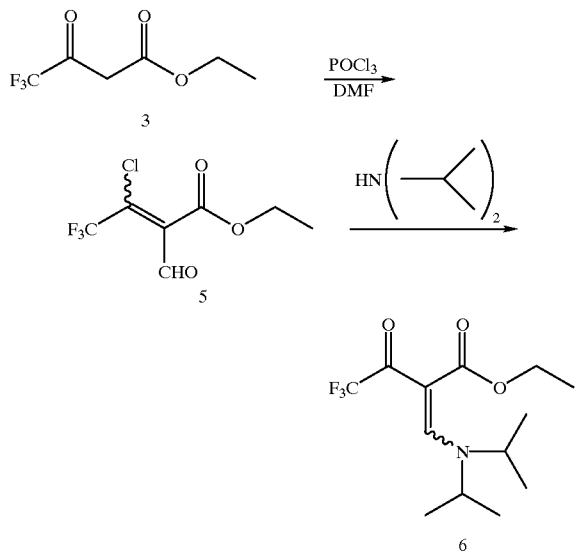

The process of the present invent avoids the problems associated with the use of POCl$_3$ and attendant disposal of associated phosphorous and chloride by-products. Moreover, since the present process is but one step, it may be run under very productive and economical conditions in a single reaction vessel.

Thus, the present invention provides a process to prepare a compound of formula (I) by the reaction of a trihaloacetyl compound of formula (II) with an acetal of formula (III) in the presence of an organic acid and an optional solvent wherein
A is an oxygen atom or a sulfur atom,
B is R, OR, N(R)$_2$ or SR,
R is a hydrogen atom, alkyl, haloalkyl, alkenyl, alkynyl, phenyl or phenyl substituted with up to three substituents independently selected from halo, alkyl and haloalkyl, or phenalkyl or phenalkyl substituted on the phenyl ring with up to three substituents independently selected from halo, alkyl and haloalkyl,
R$^1$ and R$^2$ are both alkyl or alkenyl, or together with the nitrogen atom to which they are attached form 4-morpholinyl, 1-piperidinyl, 1-pyrrolidinyl, thiomorpholin-4-yl, 1-pyrrolyl or 1-imidazolyl,
R$^3$ and R$^4$ are both alkyl, cycloalkyl, benzyl or phenethyl, or together with the carbon atom to which they are attached form 1,3-dioxan-2-yl, 1,3-dioxolan-2-yl or catech-2-yl,
X is fluoro or chloro, and the organic acid is formic, acetic, trifluoroacetic, propionic, benzoic, toluic or phenylacetic.

In this invention, the term alkyl refers to either a straight chain (C$_1$–C$_6$)alkyl such as, but not limited to, methyl, ethyl, n-propyl, n-butyl and n-hexyl or a branched chain (C$_3$–C$_6$) alkyl such as, but not limited to, isopropyl, isobutyl, sec-butyl, tert-butyl, neopentyl, isoamyl and α-methylneopentyl. Cycloalkyl is a cyclo(C$_5$–C$_6$)alkyl, such as cyclopentyl and cyclohexyl. Alkenyl means a linear (C$_3$–C$_6$)alkenyl group and includes, for example, allyl and 2-butenyl. Alkynyl means a linear (C$_3$–C$_6$)alkynyl group and includes, for example, propargyl and 2-butynyl. Halo is fluoro, chloro, bromo or iodo. Haloalkyl means a linear or branched (C$_1$–C$_6$)alkyl group substituted with one or more halo and includes, for example, trifluoromethyl, perfluoroethyl and 2,2,2-trifluoroethyl. Phenalkyl is phen(C$_1$–C$_4$) alkyl and includes, for example, benzyl and phenethyl.

In a preferred embodiment of this invention,
A is an oxygen atom,
B is R or OR,
R is a hydrogen atom, (C$_1$–C$_4$)alkyl, (C$_3$–C$_4$)alkenyl, (C$_3$–C$_4$)alkynyl, phenyl or phenyl substituted with up to three substituents independently selected from fluoro, chloro, (C$_1$–C$_2$)alkyl and halo(C$_1$–C$_2$)alkyl, or phen(C$_1$–C$_2$) alkyl or phen(C$_1$–C$_2$)alkyl substituted on the phenyl ring with up to three substituents independently selected from fluoro, chloro, halo(C$_1$–C$_2$)alkyl and (C$_1$–C$_2$)alkyl,
R$^1$ and R$^2$ are both (C$_1$–C$_4$)alkyl or (C$_3$–C$^4$)alkenyl, or together with the nitrogen atom to which they are attached form 4-morpholinyl, 1-piperidinyl, 1-pyrrolidinyl, thiomorpholin-4-yl, 1-pyrrolyl or 1-imidazolyl,
R$^3$ and R$^4$ are both (C$_1$–C$_4$)alkyl, cyclo(C$_5$–C$_6$)alkyl, benzyl or phenethyl, or together with the carbon atom to which they are attached form 1,3-dioxan-2-yl, 1,3-dioxolan-2-yl or catech-2-yl, X is fluoro or chloro, and the organic acid is formic, acetic, propionic or phenylacetic.

In a more preferred embodiment of this invention,
A is an oxygen atom,
B is OR,
R is $(C_1-C_2)$alkyl, $(C_3-C_4)$alkenyl, $(C_3-C_4)$alkynyl, phenyl, or phen$(C_1-C_2)$alkyl,
$R^1$ and $R^2$ are both $(C_1-C_4)$alkyl or $(C_3-C_4)$alkenyl, or together with the nitrogen atom to which they are attached form 4-morpholinyl, 1-piperidinyl, 1-pyrrolidinyl, thiomorpholin-4-yl, 1-pyrrolyl or 1-imidazolyl,
$R^3$ and $R^4$ are both $(C_1-C_4)$alkyl, cyclohexyl or benzyl, or together with the carbon atom to which they are attached form 1,3-dioxolan-2-yl,
X is fluoro, and the organic acid is acetic, propionic or phenylacetic.

In an even more preferred embodiment of this invention,
A is an oxygen atom,
B is OR,
R is $(C_1-C_2)$alkyl,
$R^1$ and $R^2$ are both methyl,
$R^3$ and $R^4$ are both $(C_1-C_3)$alkyl, cyclohexyl or together with the carbon atom to which they are attached form 1,3-dioxolan-2-yl,
X is fluoro, and the organic acid is acetic.

The process can be conveniently conducted at a temperature of from about 0° C. to about 150° C. or the reflux temperature of the reaction mixture, whichever is lower. Ambient temperature conditions of from about 18° C. to about 35° C. are very satisfactory. Typical reaction times at these temperatures are from about 0.5 to about 5 hours depending on the type of acetal which is used.

The reaction can be effected either in the presence or absence of a solvent. When no solvent is employed, a stoichiometric excess of the acetal can be utilized to facilitate the reaction. If a solvent is present, preferred kinds are the polar type such as, but not limited to, tetrahydrofuran, acetonitrile and 1,4-dioxane. If a non-polar solvent such as hexane is used, a two-phased system between the solvent and the reactants is produced; nevertheless, the reaction proceeds successfully using such a solvent type.

The more suitable acids are weak organic acids such as, but not limited to, formic, acetic, propionic, benzoic, toluic or phenylacetic. Although effective, the strong acids, such as trifluoroacetic acid, can produce side products which may reduce yield.

Typically, the acetal is added to a stirred mixture of the trihaloacetyl compound and the organic acid. A reverse addition procedure is also acceptable. The solvent, if employed, may be present with the acetal, the trihaloacetyl compound or both. Stoichiometrically, two equivalents of the acetal and the organic acid are required to react with one equivalent of the trihaloacetyl compound. An excess of acetal and/or organic acid is also acceptable.

Upon reaction completion, the reaction mixture is poured into water and then extracted with methylene chloride. The organic extract is washed with water, dried using a convenient drying agent such as $MgSO_4$, and concentrated to provide the compound of formula (I). The desired product can be further purified if desired by column chromatography using ethyl acetate/hexanes mixture as a typical eluant.

The following examples and Table 1 are provided to further illustrate the utilization of the invention and to provide additional guidance to the practitioner.

Table 1 compares the yields of the desired compound 2 and the by-product 4 from the reaction of ethyl trifluoroacetoacetate (ETFAA) and various DMF acetals in the presence or absence of acetic acid. It will be readily observed that with DMF dimethylacetal in the presence of acetic acid, the target compound 2 {ethyl 2-trifluoroacetyl-3-(N,N-dimethylamino)-2-propenoate} is obtained in 61.8% yield. Without the acetic acid, there is a reversal in the yield of the products with the undesired compound 4 {ethyl 3-(N,N-dimethylamino)-2-propenoate} being formed as the major product. With DMF diisopropylacetal or DMF dicyclohexylacetal in the presence of acetic acid, the target compound 2 is obtained almost exclusively. Again, in the absence of the acetic acid, the undesired compound 4 is formed as the major product.

TABLE 1

| Example No. | Equivalents of ETFAA:Acetal:HOAc | R Group of Acetal | Isolated 2 | % Yields 4 |
|---|---|---|---|---|
| 1 | 1 : 2 : 2 | methyl | 61.8 | 19.8 |
| 2 | 1 : 2 : 0 | methyl | 14.2 | 58.4 |
| 3 | 1 : 2 : 2 | isopropyl | 81.2 | trace |
| 4 | 1 : 2 : 0 | isopropyl | 19.4 | 64.1 |
| 5 | 1 : 2 : 2 | cyclohexyl | 85.0 | trace |
| 6 | 1 : 2 : 0 | cyclohexyl | 21.2 | 62.8 |

Example 1

Reaction of Ethyl Trifluoroacetoacetate with DMF Dimethyl Acetal in the Presence of Acetic Acid To a stirred mixture of ethyl trifluoroacetoacetate (4.6 g, 0.025 mol) and acetic acid (3.0 g, 0.05 mol) in 20 ml of dry tetrahydrofuran (THF), DMF dimethyl acetal (6.2 g, 0.05 mol) was added dropwise at such a rate that the reaction temperature did not exceed 35° C. After the addition, the mixture was stirred for additional 30 minutes to complete the reaction as monitored by thin layer chromatography (TLC). The yellow reaction mixture was poured into water and then extracted with $CH_2Cl_2$. The organic extract was washed with water, brine solution, and dried ($MgSO_4$). The solvent was removed by evaporation to give a yellow oil which was column-chromatographed (silica gel; $Et_2O$:Hexanes/7:3) to separate the products.

Ethyl 2-trifluoroacetyl-3-(N,N-dimethylamino)-2-propenoate (Compound 2; $R_f$:0.3) was obtained as an oil which solidified on standing; 3.7 g (61.8%). The compound was recrystallized from hexanes/EtOAc mixture to give an off-white solid; mp: 43–45° C.; $^1H$ NMR ($CDCl_3$) $\delta$ 1.3 (t, 3H); 2.9 (s, 3H); 3.3 (s, 3H); 4.4 (q, 2H); 7.3 (s, 1H). $^{19}F$ NMR ($CDCl_3$)-72 ppm.

Ethyl 3-(N,N-dimethylamino)-2-propenoate (Compound 4; $R_f$:0.5) was obtained as a brown-yellowish oil; 0.71 g (19.8%); $^1H$ NMR ($CDCl_3$) $\delta$ 1.25 (t, 3H); 2.9 (br, 6H); 4.5 (d, 1H); 7.5 (d, 1H). $^{19}F$ NMR ($CDCl_3$)-71 ppm.

Example 2
Reaction of Ethyl Trifluoroacetoacetate with DMF Dimethyl Acetal in the Absence of Acetic Acid The procedure in Example 1 was repeated, but without the addition of the acetic acid to the reaction mixture. After the work-up, the residual yellow oil was column-chromatographed on silica gel (Ether:Hexanes/7:3) to separate the products. Ethyl 3-(N,N-dimethylamino)-2-propenoate (Compound 4, $R_f$=0.5) was obtained as the major product in the form of an oil; 2.1 g (58.4%). Ethyl 2-trifluoroacetyl-3-(N,N-dimethylamino)-2-propenoate (Compound 2; $R_f$=0.3) was obtained as the minor product; 0.85 g (14.2%).

Example 3
Reaction of Ethyl Trifluoroacetoacetate with DMF Diisopropyl Acetal in the Presence of Acetic Acid To a stirred mixture of ethyl trifluoroacetoacetate (4.6 g, 0.025 mol) and acetic acid (3.0 g, 0.05 mol), DMF diisopropyl acetal (8.75 g, 0.05 mol) diluted with 5 ml of THF was added dropwise at a rate which maintained the reaction temperature below 35° C. After stirring the mixture at ambient temperature for 3 hours to complete the reaction (TLC), it was poured into water and extracted with ether. The ether extract was washed with water, brine solution, then dried ($MgSO_4$), and concentrated. The residual yellow oil was flash column-chromatographed on silica gel (Hexanes:Ethyl acetate/7:3) to give ethyl 2-trifluoroacetyl 3-(N,N-dimethylamino)-2-propenoate, (Compound 2; $R_f$=0.3) as the main product; 4.85 g (81.2%).

Only a trace quantity (TLC) of ethyl 3-(N,N-dimethylamino)-2-propenoate (Compound 4, $R_f$=0.5) was formed from this reaction.

Example 4
Reaction of Ethyl Trifluoroacetoacetate with DMF Diisopropyl Acetal in the Absence of Acetic Acid The procedure in Example 3 was repeated, but without the addition of the acetic acid to the reaction mixture. After the work-up, the residual yellow oil was column-chromatographed on silica gel (Hexanes:Ethyl acetate/7:3) to separate the products. Ethyl 3-(N,N-dimethylamino)-2-propenoate (Compound 4, $R_f$=0.5) was obtained as the major product in the form of an oil; 2.3 g (64.1%). Ethyl 2-trifluoroacetyl-3-(N,N-dimethylamino)-2-propenoate (Compound 2; $R_f$=0.3) was obtained as the minor product; 1.15 g (19.4%).

Example 5
Reaction of Ethyl Trifluoroacetoacetate with DMF Dicyclohexyl Acetal in the Presence of Acetic Acid To a stirred mixture of ethyl trifluoroacetoacetate (3.0 g, 0.016 mol) and acetic acid (2.0 g, 0.033 mol) in 25 ml of dry THF at room temperature, DMF dicyclohexyl acetal (8.5 g, 0.033 mol) was added dropwise at a rate which maintained the reaction temperature below 35° C. After stirring the mixture at ambient temperature for 2.5 hours to complete the reaction (TLC), it was poured into water and extracted with ether. The ether extract was washed with water, brine solution, then dried ($MgSO_4$), and concentrated. The residual yellow oil was column-chromatographed on silica gel (Hexanes:Ethyl acetate/7:3) to give ethyl 2-trifluoroacetyl-3-(N,N-dimethylamino)-2-propenoate (Compound 2, $R_f$=0.3) as the sole product; 3.25 g (85%).

Only a trace quantity (TLC) of ethyl 3-(N,N-dimethylamino)-2-propenoate (Compound 4, $R_f$=0.5) was formed from this reaction.

Example 6
Reaction of Ethyl Trifluoroacetoacetate with DMF Dicyclohexyl Acetal in the Absence of Acetic Acid The procedure in Example 5 was repeated, but without the addition of the acetic acid to the reaction mixture. After the work-up, the residual yellow oil was column-chromatographed on silica gel (Hexanes:Ethyl acetate/7:3) to separate the products. Ethyl 3-(N,N-dimethylamino)-2-propenoate (Compound 4, $R_f$=0.5) was obtained as the major product in the form of an oil; 1.45 g (62.8%). Ethyl 2-trifluoroacetyl-3-(N,N-dimethylamino)-2-propenoate (Compound 2; $R_f$=0.3) was obtained as the minor product; 0.8 g (21.2%).

Example 7
Reaction of Ethyl Trifluoroacetoacetate with DMF Diisopropyl Acetal in the Presence of Acetic Acid Without Solvent To a stirred mixture of ethyl trifluoroacetoacetate (4.6 g, 0.025 mol) and acetic acid (3.0 g, 0.05 mol) at room temperature, DMF diusopropyl acetal (8.75 g, 0.05 mol) was added dropwise at a rate which maintained the reaction temperature below 35° C. After stirring the mixture at ambient temperature for 2 hours to complete the reaction (TLC), it was poured into water and extracted with ether. The ether extract was washed with water, brine solution, then dried ($MgSO_4$), and concentrated. The residual yellow oil was column-chromatographed on silica gel (Hexanes:Ethyl acetate/7:3) to give ethyl 2-trifluoroacetyl-3-(N,N-dimethylamino)-2-propenoate (Compound 2; $R_f$=0.3) as the main product; 4.5 g (75%).

Example 8
Reaction of Ethyl Trifluoroacetoacetate with DMF Dimethyl Acetal in the Presence of Formic Acid To a stirred mixture of ethyl trifluoroacetoacetate (4.6 g, 0.025 mol) and formic acid (2.3 g, 0.05 mol) in 15 ml of THF, DMF dimethyl acetal (6.2 g, 0.05 mol) was added dropwise at a rate which maintained the reaction temperature below 35° C. After stirring the mixture at ambient temperature for 45 minutes to complete the reaction (TLC), it was poured into water and extracted with ether. The ether extract was washed with water, brine solution, then dried ($MgSO_4$), and concentrated. The residual yellow oil was column-chromatographed on silica gel (Hexanes:Ethyl acetate/7:3) to give ethyl 2-trifluoroacetyl-3-(N,N-dimethylamino)-2-propenoate (Compound 2; $R_f$=0.3) as the major product; 3.2 g (53%). Ethyl 3-(N,N-dimethylamino)-2-propenoate (Compound 4, $R_f$=0.5) was obtained as the minor product in the form of an oil; 0.85 g (23.7%).

I claim:

1. A process to prepare a compound of formula (I) by the reaction of a trihaloacetyl compound of formula (II) with an acetal of formula (III) in the presence of an organic acid and an optional solvent

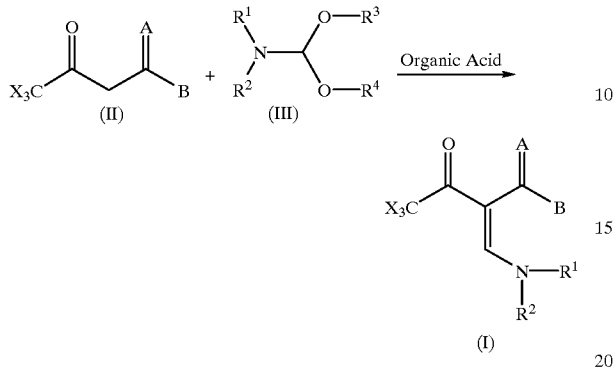

wherein
A is an oxygen atom or a sulfur atom,
B is R, OR, N(R)$_2$ or SR,
R is a hydrogen atom, alkyl, haloalkyl, alkenyl, alkynyl, phenyl or phenyl substituted with up to three substituents independently selected from halo, alkyl and haloalkyl or phenalkyl or phenalkyl substituted on the phenyl ring with up to three substituents independently selected from halo, haloalkyl and alkyl,
$R^1$ and $R^2$ are both alkyl or alkenyl, or together with the nitrogen atom to which they are attached form 4-morpholinyl, 1-piperidinyl, 1-pyrrolidinyl, thiomorpholin-4-yl, 1-pyrrolyl or 1-imidazolyl,
$R^3$ and $R^4$ are both alkyl, cycloalkyl, benzyl or phenethyl, or together with the oxygen atoms to which they are attached form 1,3-dioxan-2-yl, 1,3-dioxolan-2-yl or catech-2-yl,
X is fluoro or chloro, and
the organic acid is formic, acetic, trifluoroacetic, propionic, benzoic, toluic or phenylacetic.

2. The process of claim 1 wherein
A is an oxygen atom,
B is R or OR,
R is a hydrogen atom, $(C_1-C_4)$alkyl, $(C_3-C_4)$alkenyl, $(C_3-C_4)$alkynyl, phenyl or phenyl substituted with up to three substituents independently selected from fluoro, chloro, $(C_1-C_2)$alkyl and halo$(C_1-C_2)$alkyl, or phen$(C_1-C_2)$alkyl or phen$(C_1-C_2)$alkyl substituted on the phenyl ring with up to three substituents independently selected from fluoro, chloro, halo$(C_1-C_2)$alkyl and $(C_1-C_2)$alkyl,
$R^1$ and $R^2$ are both $(C_1-C_4)$alkyl or $(C_3-C_4)$alkenyl, or together with the nitrogen atom to which they are attached form 4-morpholinyl, 1-piperidinyl, 1-pyrrolidinyl, thiomorpholin-4-yl, 1-pyrrolyl or 1-imidazolyl,
$R^3$ and $R^4$ are both $(C_1-C_4)$alkyl, cyclo$(C_5-C_6)$alkyl, benzyl or phenethyl, or together with the oxygen atoms to which they are attached form 1,3-dioxan-2-yl, 1,3-dioxolan-2-yl or catech-2-yl,
X is fluoro or chloro, and the organic acid is formic, acetic, propionic or phenylacetic.

3. The process of claim 2 wherein
A is an oxygen atom,
B is OR,
R is $(C_1-C_2)$alkyl, $(C_3-C_4)$alkenyl, $(C_3-C_4)$alkynyl, phenyl, or phen$(C_1-C_2)$alkyl,
$R^1$ and $R^2$ are both $(C_1-C_4)$alkyl or $(C_3-C_4)$alkenyl, or together with the nitrogen atom to which they are attached form 4-morpholinyl, 1-piperidinyl, 1-pyrrolidinyl, thiomorpholin-4-yl, 1-pyrrolyl or 1-imidazolyl,
$R^3$ and $R^4$ are both $(C_1-C_4)$alkyl, cyclohexyl or benzyl, or together with the oxygen atoms to which they are attached form 1,3-dioxolan-2-yl,
X is fluoro, and the organic acid is acetic, propionic or phenylacetic.

4. The process of claim 3 wherein
A is an oxygen atom,
B is OR,
R is $(C_1-C_2)$alkyl,
$R^1$ and $R^2$ are both methyl,
$R^3$ and $R^4$ are both $(C_1-C_3)$alkyl, cyclohexyl or together with the oxygen atoms to which they are attached form 1,3-dioxolan-2-yl,
X is fluoro, and the organic acid is acetic.

5. A process to prepare ethyl 2-trifluoroacetyl-3-(N,N-dimethylamino)-2-propenoate by the reaction of ethyl trifluoroacetoacetate with an acetal of formula (III) in the presence of an organic acid and an optional solvent

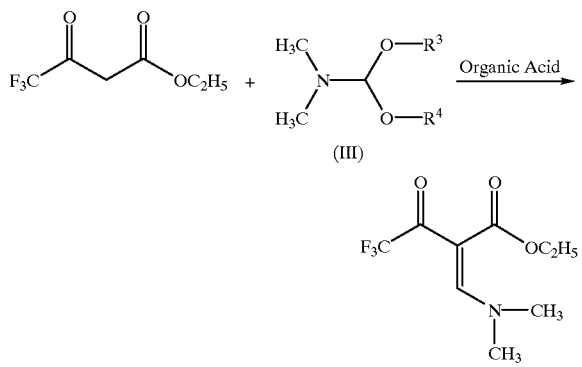

wherein
$R^3$ and $R^4$ are both alkyl, cycloalkyl, benzyl or phenethyl, or together with the oxygen atoms to which they are attached form 1,3-dioxan-2-yl, 1,3-dioxolan-2-yl or catech-2-yl and the organic acid is formic, acetic, trifluoroacetic, propionic, benzoic, toluic or phenylacetic.

6. The process of claim 5 wherein $R^3$ and $R^4$ are both $(C_1-C_4)$alkyl, cyclo$(C_5-C_6)$alkyl, benzyl or phenethyl, or together with the oxygen atoms to which they are attached form 1,3-dioxan-2-yl, 1,3-dioxolan-2-yl or catech-2-yl and the organic acid is formic, acetic, propionic or phenylacetic.

7. The process of claim 6 wherein $R^3$ and $R^4$ are both $(C_1-C_4)$alkyl, cyclohexyl or benzyl, or together with the oxygen atoms to which they are attached form 1,3-dioxolan-2-yl and the organic acid is acetic, propionic or phenylacetic.

8. The process of claim 7 wherein $R^3$ and $R^4$ are both $(C_1-C_3)$alkyl, cyclohexyl or together with the oxygen atoms to which they are attached form 1,3-dioxolan-2-yl and the organic acid is acetic.

9. The process of claim 1 or 5 which is conducted in the absence of a solvent.

10. The process of claim 1 or 5 which is conducted in a polar solvent selected from tetrahydrofuran, acetonitrile and 1,4-dioxane.

* * * * *